United States Patent [19]

McClure

[11] 4,431,647

[45] Feb. 14, 1984

[54] METHOD OF USE OF ENANTIOMERS OF TRANS-INDENO[1,2-B]-1,4-OXAZINES

[75] Inventor: David E. McClure, Lansdale

[73] Assignee: Merck & Co., Inc., Rahway, N.J.

[21] Appl. No.: 404,104

[22] Filed: Aug. 2, 1982

Related U.S. Application Data

[63] Continuation-in-part of Ser. No. 323,350, Nov. 20, 1981, abandoned.

[51] Int. Cl.³ .......................................... A61K 31/535
[52] U.S. Cl. .......................... 424/248.58; 424/248.4; 544/101
[58] Field of Search .................... 544/101; 424/248.4, 424/248.58

[56] References Cited

U.S. PATENT DOCUMENTS 3,642,789  2/1972  Faith et al. .................... 269/244 R

OTHER PUBLICATIONS

McClure et al., J. Org. Chem., 46, 2431 (1981).
Craig et al., J. Org. Chem., 39, 1669 (1974).

Primary Examiner—Richard Raymond
Attorney, Agent, or Firm—William H. Nicholson; Mario A. Monaco

[57] ABSTRACT

The (R,R)-enantiomers of trans-indeno[1,2-b]-1,4-oxazines demonstrate dopaminergic activity, whereas the (S,S)-enantiomers demonstrate α-adrenergic antagonist activity. They are prepared by cyclization of the appropriate chiral 2-amino-1-hydroxyindane.

2 Claims, No Drawings

METHOD OF USE OF ENANTIOMERS OF TRANS-INDENO[1,2-B]-1,4-OXAZINES

BACKGROUND OF THE INVENTION

This is a continuation-in-part of co-pending application, Ser. No. 323,350, filed Nov. 20, 1981 now abandoned.

This invention is concerned with the enantiomers of trans-2,3,4,4a,5,9b-hexahydroindeno[1,2-b]-1,4-oxazines of structural formula I which is used in this disclosure to depict the racemic, (S,S)- and (R,R)-enantiomers unless a specific entity is meant in which case it is specified to be racemic, or one of the optical isomers.

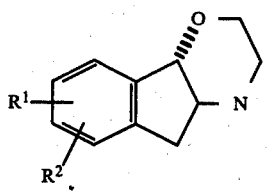

The (R,R)-enantiomer demonstrates the dopaminergic activity of antiparkinson agents, whereas the (S,S)-enantiomer demonstrates the α-adrenergic receptor antagonism of antidepressant agents.

The racemic compound is described by Faith et al. in U.S. Pat. No. 3,642,789 where it is alleged to have antidepressant activity by virtue of its reserpine antagonism and amphetamine agonism.

Surprisingly it is now found that the (S,S)-enantiomer has only antidepressant activity. Even more surprisingly, it is found that the optical antipode, the (R,R)-enantiomer has a somewhat opposite effect on the CNS being an antiparkinson agent.

It is therefore an object of this invention to provide the pure (R,R)- and (S,S)-enantiomers of compound I, processes for preparing the pair of compounds, pharmaceutical formulations, and methods of treating depression with the (S,S)-enantiomer or its pharmaceutical compositions, and methods of treating Parkinsonism with the (R,R)-enantiomer or its pharmaceutical compositions.

DETAILED DESCRIPTION OF THE INVENTION

The novel compounds of this invention are the (R,R)-, and (S,S)-enantiomer, each substantially free of the other, of the compound of structural formula:

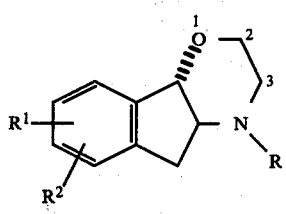

or a pharmaceutically acceptable salt thereof, wherein
R is hydrogen; branched or unbranched $C_{1-4}$ alkyl, especially methyl, ethyl or propyl; $C_{2-5}$ alkenyl, especially allyl; or phenyl-$C_{1-4}$ alkyl, especially benzyl; and
$R^1$ and $R^2$ are independently hydrogen, hydroxy, or $C_{1-4}$ alkoxy, especially methoxy, or ethoxy.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

These salts are readily prepared by mixing solutions of equimolecular amounts of the free base compound and the desired acid in suitable solvents such as water, alcohols, ether or chloroform, followed by recovery of the product by collecting the precipitated salt or evaporation of the solvent.

The process for preparing the novel compounds is another embodiment of this invention and is represented as follows:

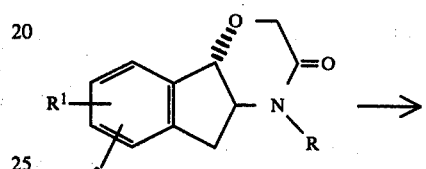

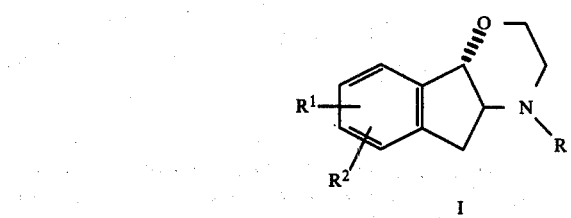

The novel process comprises the reduction of the oxazinone, II, with a metal hydride such as borane, in an inert organic solvent such as an ether, for example, tetrahydrofuran, 1,2-dimethoxyethane, tetrahydropyran, or the like at a temperature between about 0° C. and 100° C. Operating procedures normally involve slow addition of the ketone to the reducing agent at room temperature or below, followed by heating to an elevated temperature within the stated range, preferably, the reflux temperature of the solvent, for about ½ to about 4 hours usually about 1–2 hours.

A third embodiment of this invention is the pharmaceutical formulations comprising one of the novel compounds as active ingredient. They may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg, and preferably from 5 to 250 mg.

Other embodiments of this invention are the treatment of depression with the (S,S)-enantiomer and Parkinsonism with the (R,R)-enantiomer of the novel compounds. The route of administration can be oral, rectal, intravenous, intramuscular, or subcutaneous. Doses of 1.0 to 200 mg/kg/day and preferably of 5.0 to 100 mg/kg day of either active ingredient to demonstrate its respective utility are generally adequate, and if preferred it can be administered in divided doses given two to four times daily.

It is to be noted that the precise unit dosage form and dosage level depend upon the requirements of the individual being treated, and consequently are left to the discretion of the therapist.

EXAMPLE 1 trans-4-methyl 2,3,4,4a,5,9b-hexahydroindeno[1,2-b]-1,4-oxazines

Step A: Preparation of trans-2-(N-methyl-N-acetoacetylamino)-1-indanol (IV)

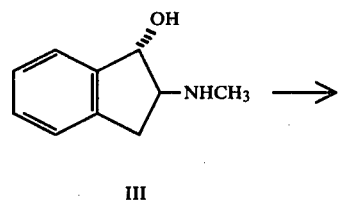

III

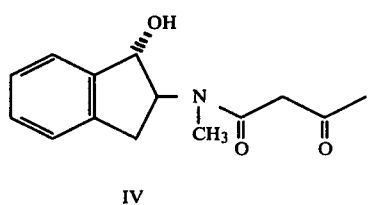

IV

To a solution of trans-2-methylamino-1-indanol (4.9 g, 0.03 m) in 100 ml of ethanol was added 2.8 g (0.033 m) of diketene. After stirring about 1 hour the mixture was concentrated to dryness in vacuo. The residue was dissolved in acetonitrile and the solvent was evaporated in vacuo to 6.3 g (85%) of an oily residue which was used directly in the next step.

Step B: Preparation of trans-2-(N-methyl-N-diazoacetoacetylamino)-1-indanol (V)

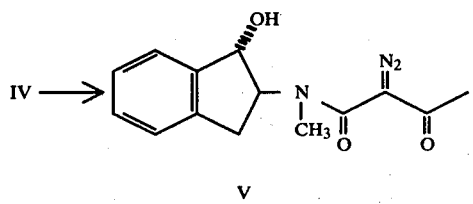

V

A mixture of the oily residue of compound IV from Step A, 100 ml of acetonitrile and 9.0 g (0.031 m) of p-carboxybenzenesulfonyl azide was cooled in ice and treated all at once with 9.0 ml (9.15 g, 0.06 m) of 1,8-diazabicyclo [5.4.0] undec-7-ene (DBU) with stirring. A homogeneous solution formed quickly followed by precipitation. The ice-bath was removed and stirring was continued for about 4 hours. Water was added and the mixture was extracted with methylene chloride (3X). The methylene chloride extract was back washed with water (2X), dried over anhydrous sodium sulfate and concentrated to dryness in vacuo leaving a residue of 7.0 g of compound V which was used directly in the next step without purification.

Step C: Preparation of 2-(N-diazoacetyl-N-methyl)amino-1-indanol (VI)

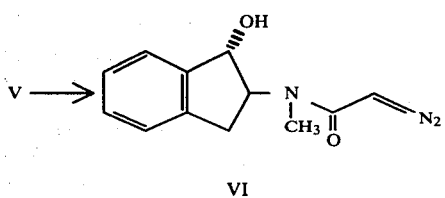

VI

The residue of structure V from Step B in 100 ml of acetonitrile was treated with 50 ml of 5% (w/v) aqueous sodium hydroxide and the mixture was stirred 5 hours at room temperature. The mixture was partitioned between added water and methylene chloride and the phases were separated. The aqueous phase was extracted again with methylene chloride and the combined methylene chloride layers were dried over anhydrous sodium sulfate. Concentration to dryness gave 4.55 g of racemic compound VI, m.p. 142°–145° C.

Step D: Preparation of trans-4-methyl-4,4a,5,9b-tetrahydroindeno[1,2-b]-1,4-oxazin-3-(2H)-one (II)

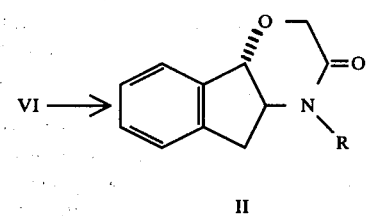

II

To a solution of 4.45 g (0.019 m) of 2-(N-diazoacetyl-N-methyl)amino-1-indanol in 200 ml of methylene chloride cooled in an ice-bath there was added dropwise 3.4 g (2.9 ml, 0.023 m) of boron trifluoride etherate. Gas evolution began immediately and the mixture was stirred for 30 minutes. Hydrochloric acid (100 ml of 1 N) was added and stirring was continued for another 30 minutes. The layers were separated and the methylene chloride layer was washed with saturated aqueous sodium bicarbonate solution and water, dried over anhydrous sodium sulfate and concentrated to dryness to give 3.3 g (84%) of racemic compound II, m.p. 154°–162° C.

Step E: Preparation of trans-4-methyl-2,3,4,4a,5,9b-hexahydroindeno[1,2-b]-1,4-oxazine (I)

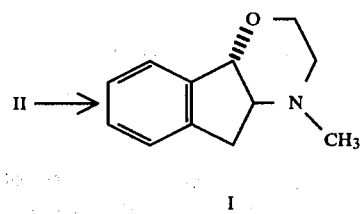

I

To a solution of 3.3 g (0.016 m) of II in 50 ml of tetrahydrofuran (THF) was added 32 ml (0.032 m) of borane (as 1 M BH₃/THF) with ice cooling. The mixture was refluxed 1 hour, cooled, treated with 50 ml of 6 N hydrochloric acid and heated on a steam bath until the THF had evaporated. After cooling the mixture was washed with ether, made basic with 40% (w/v) aqueous sodium hydroxide and extracted with methylene chloride. The extract was dried and concentrated to dryness in vacuo to give 2.4 g (42% overall for 5 steps) of racemic Compound I. Conversion to the hydrochloride gave trans-racemic I.HCl.1/4H$_2$O: m.p. 252°–255° C.

Employing the procedures substantially as described in Example 1, Steps A through E, but substituting for the starting material used in Step A thereof, an equimolar amount of the (S,S)-, or (R,R)-enantiomer of trans-2-methylamino-1-indanol, there was prepared in comparable yield: trans-(S,S)-I.HCl: m.p. 275°–278° C., $[\alpha]_D^{25}+19.42°$ (C, 0.556 MeOH); trans-(S,S)-I.maleate: m.p. 146°–150° C.; and trans-(R,R)-I.HCl: m.p. 260°–268° C., $[\alpha]_D^{25}-20.38$(C, 0.52 MeOH)

Employing the procedure substantially as described in Example 1, Steps A through E, but substituting for the trans-2-methylamino-1-indanol used as starting material in Step A an equimolecular amount of the substituted-trans-2-amino-1-indanols described in Table I there are produced corresponding amounts of the substituted trans-2,3,4,4a,5,9b-hexahydroindeno[1,2-b]-1,4-oxazines also described in Table I, in accordance with the following reaction scheme:

TABLE I

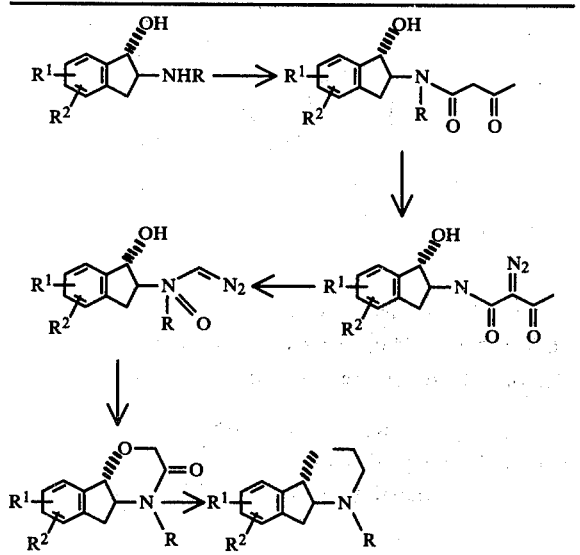

| Enantiomer | R | R$^1$ | R$^2$ | |
|---|---|---|---|---|
| racemic | —C$_2$H$_5$ | 8-OCH$_3$ | H | (m.p. |
| (R,R) | —C$_2$H$_5$ | 8-OCH$_3$ | H | 243–245° C., |
| (S,S) | —C$_2$H$_5$ | 8-OCH$_3$ | H | as HCl salt) |
| (R,R) | —n-C$_4$H$_9$ | H | H | |
| (S,S) | —n-C$_4$H$_9$ | H | H | |
| (R,R) | —CH$_2$C$_6$H$_5$ | H | H | |
| (S,S) | —CH$_2$C$_6$H$_5$ | H | H | |
| (R,R) | —C$_2$H$_5$ | 8-OCH$_3$ | 7-OCH$_3$ | |
| (S,S) | —C$_2$H$_5$ | 8-OCH$_3$ | 7-OCH$_3$ | |
| (R,R) | i-C$_3$H$_7$ | 7-OC$_2$H$_5$ | 6-OC$_2$H$_5$ | |
| (S,S) | i-C$_3$H$_7$ | 7-OC$_2$H$_5$ | 6-OC$_2$H$_5$ | |
| (R,R) | —CH$_2$CH=CH$_2$ | H | H | |
| (S,S) | —CH$_2$CH=CH$_2$ | H | H | |

EXAMPLE 2 trans-4-ethyl-6-hydroxy-2,3,4,4a,5,9b-hexahydroindeno-[1,2-b]-1,4-oxazine hydrobromide Step A: Preparation of 4-(phenylmethoxy)-1-indanone (VII)

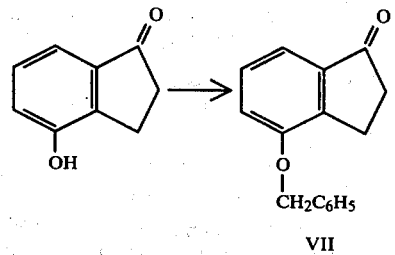

To a solution of 4.44 g (0.03 m) of 4-hydroxy-1-indanone in 50 ml of dimethylformamide is added 4.15 g (0.03 m) of potassium carbonate with stirring followed by the dropwise addition of 3.8 g (0.03 m) of benzyl chloride. The reaction mixture is heated at steam bath temperature for 3 hours, then cooled and diluted with water. The aqueous mixture is extracted with ethyl acetate and the extract is washed with water, dried over anhydrous sodium sulfate and concentrated to dryness in vacuo. The residue is triturated with ether and concentrated to dryness to yield: 5.86 g (82%) of a brown solid, m.p. 70°–73° C., sufficiently pure to be used in the next step.

Step B: Preparation of 2-(hydroxyimino)-4-(phenylmethoxy)-1-indanone

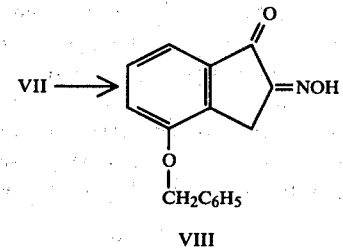

To an ice-cooled solution of 1.91 g (0.008 m) of 4-(phenylmethoxy)-1-indanone in 75 ml of anhydrous ether is added dropwise with stirring 1.2 ml (0.088 m) of isoamyl nitrite while hydrogen chloride is simultaneously bubbled in. After stirring at room temperature for twenty minutes, the reaction mixture is partially concentrated and the solid which separates is filtered to yield 1.83 g (86%) of material sufficiently pure to be used in the next step.

Step C: Preparation of 2-(acetylamino)-4-hydroxy-1-indanone

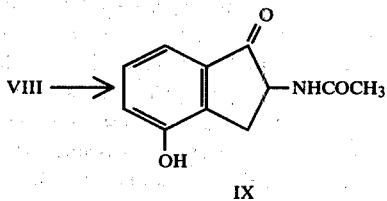

A suspension of 4.94 g (0.018 m) of 2-(hydroxyimino)-4-(phenylmethoxy)-1-indanone in 35 ml each of glacial acetic acid and acetic anhydride containing 0.7 g of 10% palladium on carbon catalyst is hydrogenated at room temperature until two equivalents of hydrogen are used. The catalyst is filtered off, washed with methanol, and the combined acetic acid-alcohol filtrate is concentrated to dryness in vacuo. The residue is triturated with ethanol and the solid which is filtered is a roughly equal mixture of the 4-hydroxy and 4-(phenylmethoxy) compounds. The mixture is taken up in aqueous sodium hydroxide and the 4-(phenylmethoxy) compound is extracted with ethyl acetate. The basic solution is acidified with aqueous hydrochloric acid and extracted with ethyl acetate. The extract is dried over anhydrous sodium sulfate and concentrated to dryness in vacuo to yield the 4-hydroxy compound.

Step D: Preparation of 2-acetylamino-4-(methylthiomethoxy)-1-indanone (X)

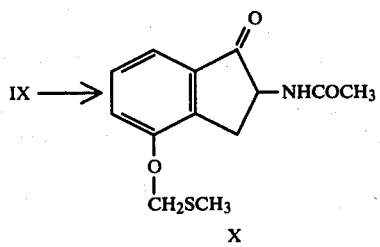

To 2-acetylamino-4-hydroxy-1-indanone 10.25 g (0.05 m) in 50 ml of dry HMPA under $N_2$ is added 2.6 g (0.055 m) of a 50% oil dispersion of sodium hydride in portions. After stirring at room temperature for ½ hr, 5.3 g (0.055 m) of chloromethyl methyl sulfide is added, and the mixture is stirred overnight. Water is added and the mixture is extracted with ethyl acetate which is back-washed with water. After drying ($Na_2SO_4$) and concentration, the desired product is obtained.

Step E: Preparation of trans-2-ethylamino-4-(methylthiomethoxy)-1-indanol (XI)

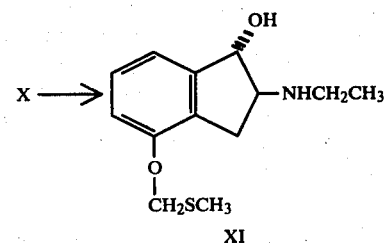

The residue from Step D is dissolved in 50 ml of THF and added to 3.8 g (0.1 m) of $LiAlH_4$ in 50 ml of THF dropwise. The mixture is refluxed for one hour after completion of the addition. The mixture is cooled and sufficient saturated aqueous $Na_2SO_4$ solution is added to quench the excess $LiAlH_4$. Methylene chloride and solid anhydrous $Na_2SO_4$ is added and the mixture is filtered. Concentration provides the crude product.

Step F: Preparation of trans-2-(N-ethyl-N-acetoacetylamino)-4-(methylthiomethoxy)-1-indanol (XII)

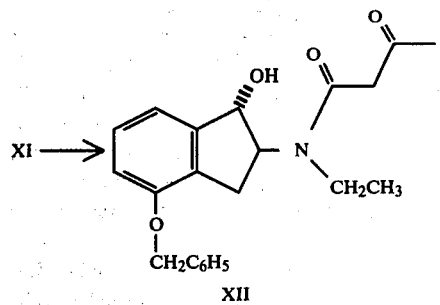

Using the product from Step E and following the procedure of Example 1, Step A, with 4.6 g (0.055 m) of diketone in 200 ml ethanol, the desired product is obtained.

Step G: Preparation of trans-2-(N-ethyl-N-diazoacetoacetylamino)-4-(methylthiomethoxy)-1-indanol (XIII)

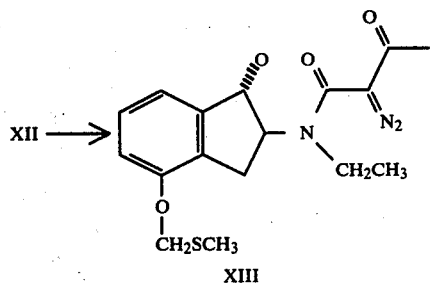

Using the product in Example 1, Step B, with 11.3 g (0.05 m) of p-carboxybenzenesulfonylazide in 150 ml of acetonitrile, the desired product is obtained.

Step H: Preparation of trans-2-(N-ethyl-N-diazoacetylamino)-4-(methylthiomethoxy)-1-indanol (XIV)

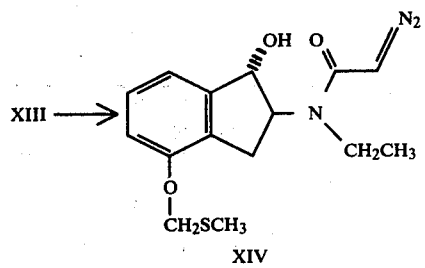

Using the product from Step G and following the procedure in Example 1, Step C, with 100 ml of acetonitrile and 50 ml of 5% (w/v) aqueous sodium hydroxide and stirring overnight, the desired product is obtained.

Step I: Preparation of trans-4-ethyl-6-(methylthiomethoxy)-4,4a,5,9b-tetrahydroindeno[1,2-b]-1,4-oxazin-3-(2H)-one (XV)

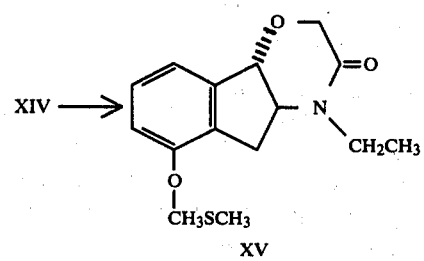

Using the product from Step H and following the procedure in Example 1, Step D, with 6.4 g (5.5 ml, 0.045 m) of boron trifluoride etherate in 200 ml of methylene chloride, the desired product is obtained.

Step J: Preparation of trans-4-ethyl-6-hydroxy-4,4a,5,9b-tetrahydroindeno[1,2-b]-1,4-oxazin-3-(2H)-one (XVI)

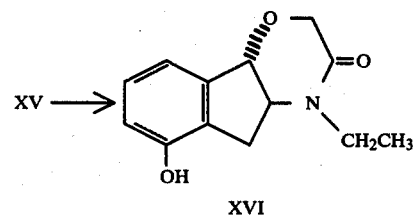

To the product from Step I in 200 ml of a 4:1 (v/v) acetonitrile-water mixture is added 12.2 g (0.045 m) of mercuric chloride. The resulting suspension is refluxed for 10 hr, diluted with methylene chloride, and filtered through celite. The organic phase is washed with water, dried over $Na_2SO_4$, and concentrated. The residue is taken up in methanol, aqueous 48% HBr is added, and the solvents are removed in vacuo. Methanol is added and the mixture reconcentrated several times to remove any water. Ethanol is added and ether is used to precipitate the desired HBr salt of the product.

Step K: Preparation of trans-4-ethyl-6-hydroxy-2,3,4,4a,5,9b-hexahydroindeno[1,2-b]-1,4-oxazine (I)

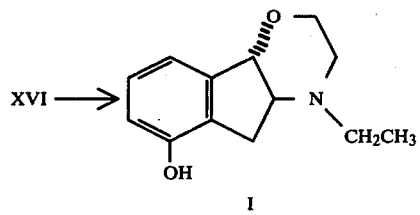

Using the product from Step J and following the procedure in Example 1, Step E, with 45 ml (0.045 m) of borane (as a 1 M $BH_3$/THF solution) in 100 ml of THF, the desired product is obtained.

If compound XI, the product of Step E, is resolved into its (R,R)- and (S,S)-enantiomers and each is independently subjected to the chemical reactions described in Steps F through K, there are produced respectively, the (R,R)- and (S,S)-enantiomers of trans-4-ethyl-6-hydroxy-2,3,4,4a,5,9b-hexahydroindeno[1,2-b]-1,4-oxazine.

Employing the procedures substantially as described in Example 2, Steps A through K but substituting for the starting material used therein equimolecular amounts of the hydroxy-1-indanones described in Table II, there are produced the racemic, (R,R)- and (S,S)-enantiomers of the substituted trans-2,3,4,4a,5,9b-hexahydroindeno[1,2-b]-1,4-oxazines, also described in Table II.

TABLE II

| $R^1$ | $R^2$ | R | $R^1$ | $R^2$ |
|---|---|---|---|---|
| 4-OH | | $-C_2H_5$ | 6-OH | |
| 4-OH | 5-OH | $-C_2H_5$ | 6-OH | 7-OH |
| 6-OH | | $-C_2H_5$ | 8-OH | |
| 5-OH | 6-OH | $-C_2H_5$ | 7-OH | 8-OH |
| 4-OH | | $n-C_3H_7$ | 6-OH | |
| 4-OH | | $-n-C_4H_9$ | 6-OH | |
| 7-OH | | $-C_2H_5$ | 9-OH | |

EXAMPLE 3

Pharmaceutical Composition

A typical tablet containing 100 mg of active ingredient per tablet is prepared by mixing together with the active ingredient, calcium phosphate, lactose and starch in the amounts shown in the table below. After these ingredients are thoroughly mixed, the appropriate amount of magnesium stearate is added and the dry mixture blended for an additional three minutes. This mixture is then compressed into tablets.

| Tablet Formula | |
|---|---|
| Ingredient | Mg. per Tablet |
| Trans-(R,R)-4-methyl-2,3,4,4a,5,9b-hexahydroindeno[1,2-b]-1,4-oxazine | 100 mg |
| Calcium phosphate | 52 mg |
| Lactose | 60 mg |
| Starch | 10 mg |
| Magnesium Stearate | 1 mg |

Similarly prepared are tablets comprising as active ingredient any of the other novel compounds described herein.

What is claimed is:

1. A method of treating parkinsonism which comprises the administration to a patient in need of such treatment of an effective antiparkinson amount of the (R,R)-enantiomer substantially free of the (S,S)-enantiomer of a compound of structural formula:

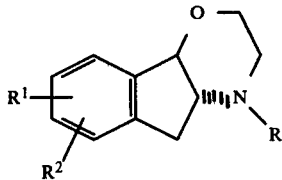

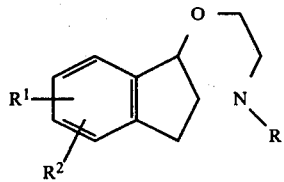

(R,R)-enantiomer or a pharmaceutically acceptable salt thereof, wherein R is $C_{1-4}$alkyl, $C_{2-5}$alkenyl or phenyl-$C_{1-4}$alkyl; and $R^1$ and $R^2$ are independently hydrogen, hydroxy or $C_{1-4}$alkoxy.

2. The method of claim 1 wherein R is methyl, ethyl or propyl, and $R^1$ and $R^2$ are independently hydrogen, hydroxy or methoxy.

* * * * *

(R,R)-enantiomer or a pharmaceutically acceptable salt thereof, wherein R is $C_{1-4}$alkyl, $C_{2-5}$alkenyl or phenyl-$C_{1-4}$alkyl; and $R^1$ and $R^2$ are independently hydrogen, hydroxy or $C_{1-4}$alkoxy.

2. The method of claim 1 wherein R is methyl, ethyl or propyl, and $R^1$ and $R^2$ are independently hydrogen, hydroxy or methoxy.

* * * * *

UNITED STATES PATENT AND TRADEMARK OFFICE
CERTIFICATE OF CORRECTION

PATENT NO. : 4,431,647

DATED : February 14, 1984

INVENTOR(S) : David E. McClure

It is certified that error appears in the above—identified patent and that said Letters Patent is hereby corrected as shown below:

Delete Column 12.

Signed and Sealed this

Twenty-second Day of May 1984

[SEAL]

Attest:

GERALD J. MOSSINGHOFF

Attesting Officer

Commissioner of Patents and Trademarks